(12) United States Patent
Daykin

(10) Patent No.: US 7,452,711 B2
(45) Date of Patent: Nov. 18, 2008

(54) CONTACT PLATE

(76) Inventor: Victor Daykin, 253 Bedford Park Avenue, Toronto, Ontario (CA) M5M 1J6

( * ) Notice: Subject to any disclaimer, the term of this patent is extended or adjusted under 35 U.S.C. 154(b) by 16 days.

(21) Appl. No.: 11/124,210

(22) Filed: May 9, 2005

(65) Prior Publication Data

US 2006/0252299 A1     Nov. 9, 2006

(51) Int. Cl.
     *C12M 1/34*     (2006.01)
(52) U.S. Cl. ............................ 435/288.3; 435/305.4
(58) Field of Classification Search ... 435/288.3–288.5, 435/305.1–305.4, 309.4; 220/288, 293; 215/211, 215/214, 329; 422/102
See application file for complete search history.

(56) References Cited

U.S. PATENT DOCUMENTS

| | | | |
|---|---|---|---|
| 3,649,463 A | 3/1972 | Buterbaugh | |
| D238,886 S * | 2/1976 | Goy | D24/224 |
| 5,725,123 A | 3/1998 | Otto-Nagels | |
| 5,856,176 A | 1/1999 | Mathus et al. | |
| 6,602,704 B1 * | 8/2003 | Maxwell et al. | 435/305.4 |
| 6,969,606 B2 * | 11/2005 | Minton | 435/288.3 |
| 6,969,607 B2 * | 11/2005 | Minton | 435/288.3 |

* cited by examiner

*Primary Examiner*—Khiem Nguyen

(57) ABSTRACT

A contact plate for growing cell cultures, bacteria cultures, and the like, comprising a base and a cover. The base has a bottom wall for holding the culture medium and the like, and a circumferential sidewall extending upwardly from the bottom wall and attached thereto. The base further incorporates a flange extending outwardly from the outer periphery of the sidewall. The cover has a top wall, which has a larger diameter than the base sidewall, and a circumferential sidewall extending downwardly from the top wall and attached thereto. The contact plate has a locking means for securely holding the cover to the base of the contact plate in the locked position, wherein the locking means comprises an inter-engaging rib and groove arrangement.

7 Claims, 6 Drawing Sheets

CONTACT PLATE

FIELD OF THE INVENTION

The present invention relates to contact plates, and more particularly to contact plates which have a means for releasably locking the cover to the base.

BACKGROUND OF THE INVENTION

Contact plates, also known as culture dishes or Petri dishes, are widely known and used in laboratories for growing cell cultures, bacteria cultures, and the like. Conventional contact plates are comprised of two parts: (1) a base, which is typically a shallow open-ended cylindrical container; and (2) a cover, which is wider in diameter than the base, and fits over and covers the base.

Conventional contact plates are difficult for the user to lift and move because the cover is wider in diameter than the base and is loosely positioned over the base. In particular, the user must ensure that he or she has a firm grasp on both the base and the cover when lifting and moving the contact plate. Accordingly, either both hands are required to grasp and lift the contact plate, or the user must slide the entire contact plate off the edge of the working surface to grasp the contact plate. Alternatively, in order to lift and support the base, the user must tilt the contact plate to facilitate the positioning of his or her fingers underneath the base. This is undesirable because the tilting can shift and disturb the contents of the contact plate. Tilting of the contact plate may also cause the cover to slide; thus, making it awkward for the user to get a firm grasp on the contact plate.

Conventional contact plates are prone to accidental or inadvertent opening which may contaminate the culture. Conventional contact plates are often stacked together on the working surface, in the incubator, or in the storage area for space efficiency. As the cover of a conventional contact plate is loosely positioned over the base, the cover can be accidentally opened when the stacked contact plates are handled. In addition, the cover of a contact plate may open if the contact plate is jostled during handling. Thus, it is highly desirable to have contact plates which prevent accidental openings.

Various contact plates have been provided in which the cover is placed over the base in a snug or tight fit. However, this leads to inefficiency as the user must use both hands to open and remove the cover.

Various contact plates have been provided in the prior art, which attempt to create handles on the contact plate to facilitate the lifting of the contact plate from the work surface. U.S. Pat. No. 3,649,463 discloses a Petri dish with a handle portion extending around the outer surface of the base. U.S. Pat. No. 5,856,176 discloses a culture dish with a pair of handles extending from the base, the cover, or both. However, contact plates with external handles take up more space on the work surface, in the incubator, and in the storage area. Since a large number of contact plates are typically used at one time, this decreases the efficiency of the laboratory as fewer culture dishes can be used at a time.

Contact plates have been provided in the prior art, which attempt to create a mechanism for securely positioning the cover over the base. U.S. Pat. No. 5,725,123 discloses a cover with individual elevations on the inner surface of the cover apron, which press against the outer surface of the base wall to secure the cover to the container. However, this is not a reliable method for securing the cover to the base because the cover is only frictionally held to the base. Over time, the shape of the cover or container may change and affect the ability of the individual elevations to contact the base wall.

SUMMARY OF THE INVENTION

It is an object of the present invention to provide an improved contact plate, wherein the cover can be reliably and securely held to the base to avoid the accidental opening of the cover. It is a further object of the present invention to provide a contact plate which can be lifted and manipulated by gripping the base or the cover.

It is an object of the present invention to provide a contact plate in which the cover can be opened and removed with one hand, as well as replaced and locked with one hand. It is a further object of the present invention to provide a contact plate which can easily and efficiently be lifted and moved with one hand.

It is an object of the present invention to provide a contact plate, which can be efficiently and reliably stacked together, and can prevent the cover from being accidentally separated from the base.

The present invention is directed to a contact plate comprising a base and a cover. The base has a bottom wall for holding the culture medium and the like, and a circumferential sidewall extending upwardly from the bottom wall and attached thereto. The base further incorporates a flange extending outwardly from the outer periphery of the sidewall. The cover has a top wall, which has a larger diameter than the base sidewall, and a circumferential sidewall extending downwardly from the top wall and attached thereto. The cover and base have a locking means for securely holding the cover to the base of the contact plate in the locked position, wherein the locking means comprises an inter-engaging rib and groove arrangement.

BRIEF DESCRIPTION OF THE DRAWINGS

Preferred embodiments of the invention are shown in the drawings, wherein.

DETAILED DESCRIPTION OF THE PREFERRED EMBODIMENTS

Figure 1:
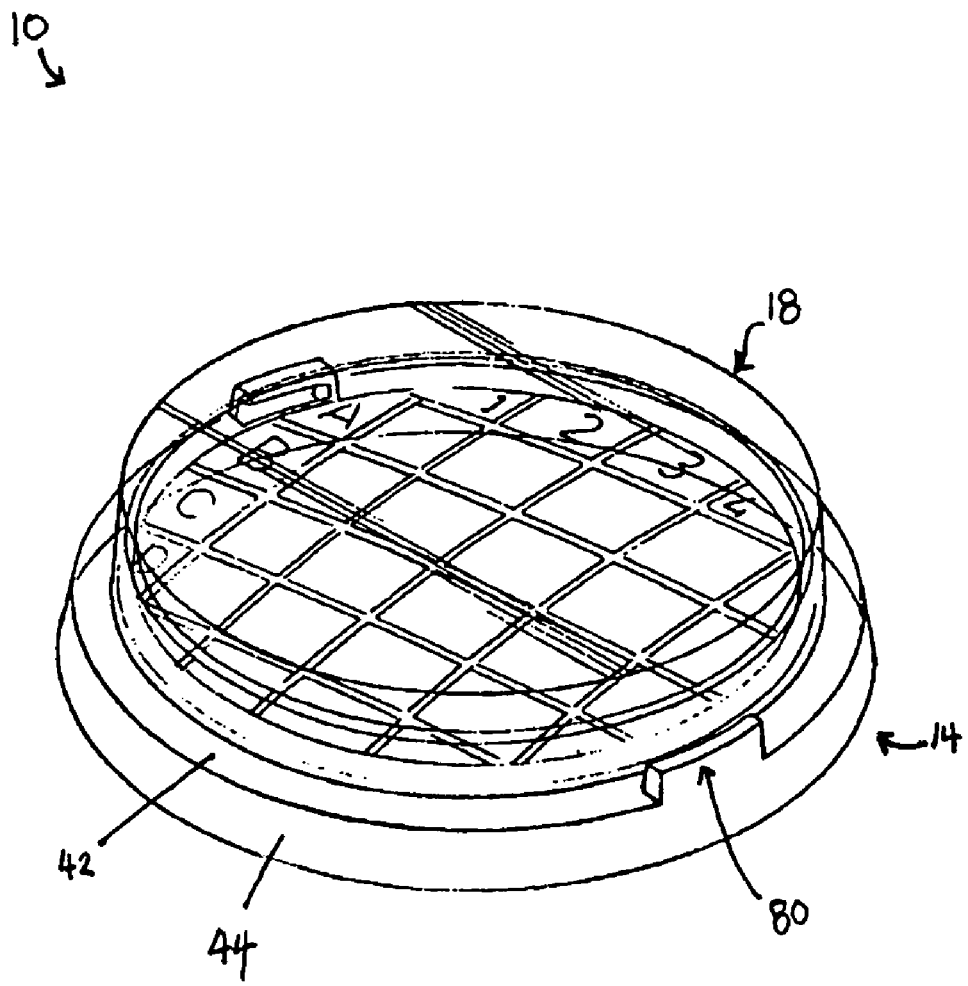
FIG. 1 is a perspective view of the contact plate of the present invention with the cover and base secured together.

With reference to FIGS. 1 to 6, a contact plate is generally indicated with the numeral (10). The contact plate (10) of the present invention includes a base (14) and a cover (18). The contact plate (10) is preferably fabricated from a plastic material. However, it can be appreciated that other suitable materials can be used. At least the cover (18), but preferably both the cover (18) and the base (14), is fabricated of a transparent material to enable the user to view the contents of the contact plate. It can also be appreciated that the size of the contact plate is not limited to any specific dimensions.

The base (14) includes a bottom wall (22) and a side wall (26), which extends upward from the bottom wall (22) and extends continuously along its entire periphery, to form an upward facing receptacle (30) for holding the culture medium and the like. Preferably, the base (14) is formed from an unitary integrally molded piece of plastic wherein the bottom wall (22) is integrally formed with the side wall (26). The side wall (26) is comprised of a outer surface area (34) and an inner surface area (38). The bottom wall (22) may be provided with suitable lines or a grid, as shown in the figures, so as to facilitate the counting of the culture in the conventional manner.

The base (14) provides at least one flange (42) extending outwardly from the outer surface area (34) of the side wall (26) and attached thereto. The flange (42) is preferably integrally formed with the side wall (26) and has a flange surface (43). In a preferred embodiment of the invention, as shown in the figures, the flange (42) extends outwardly from the outer surface area (34) of the side wall (26) and extends continuously along the entire periphery. Surrounding the contact plate (10) and extending downwardly from the perimeter of the flange (42) is a short skirt (44), which may serve as a surface for gripping and manipulating the contact plate.

The cover (18) has a top wall (46) and a side wall (50), which extends downwardly from the top wall (46) and extends continuously along its entire periphery. Preferably, the cover (18) is formed from a unitary integrally molded piece of plastic wherein the top wall (46) is integrally formed with the side wall (50). The side wall (50) has an outer surface area (56) and an inner surface area (60).

Figure 2:
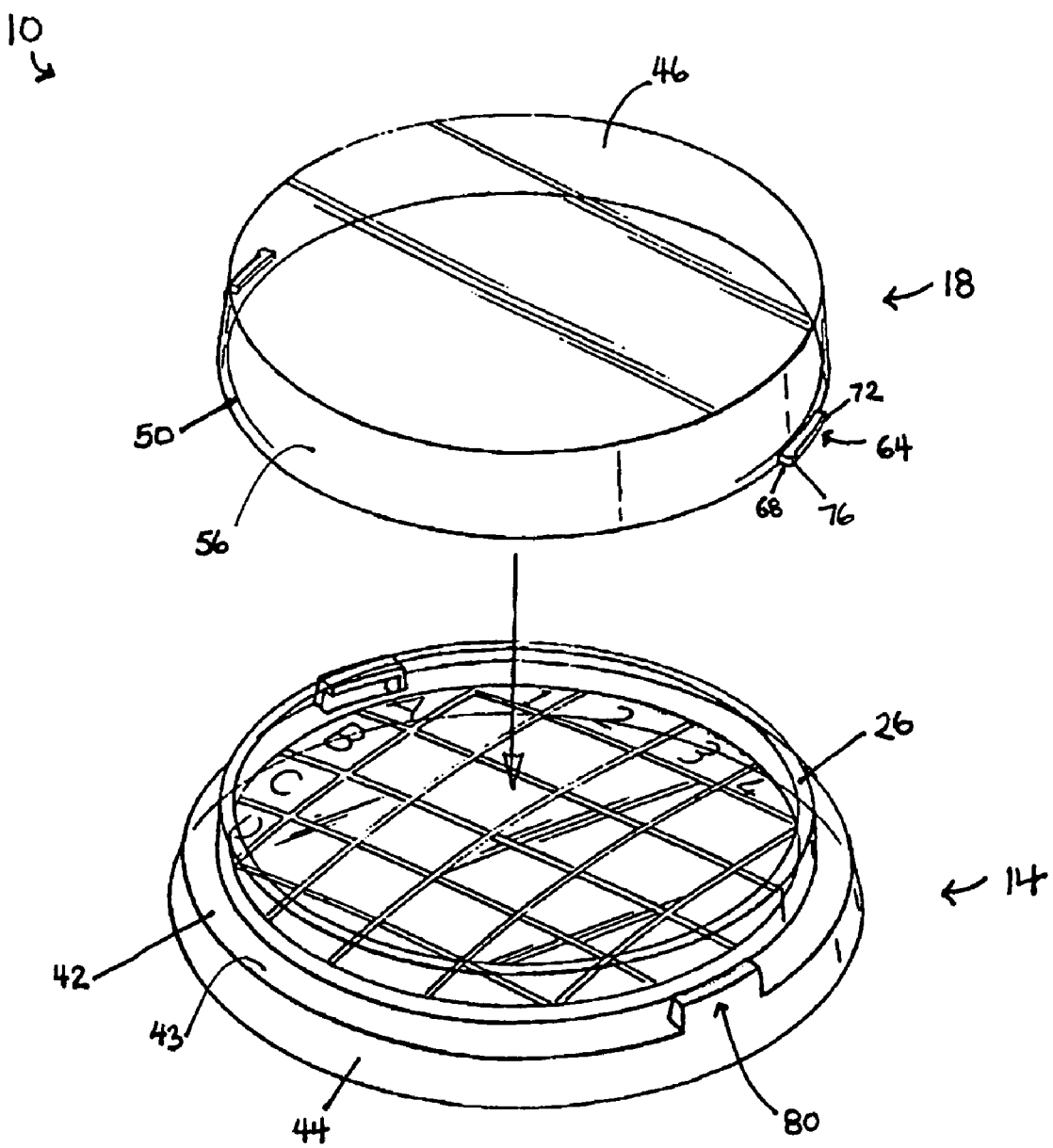
FIG. 2 is a perspective view of the contact plate of FIG. 1 with the cover separated from the base.
Figure 3:
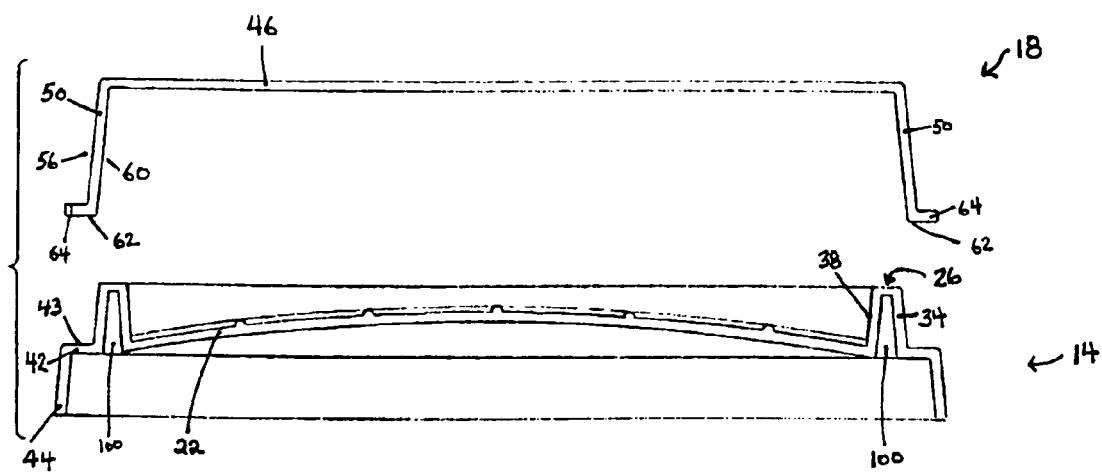
FIG. 3 is a cross-sectional side view of the contact plate of FIG. 1 with the cover separated from the base.
Figure 4:
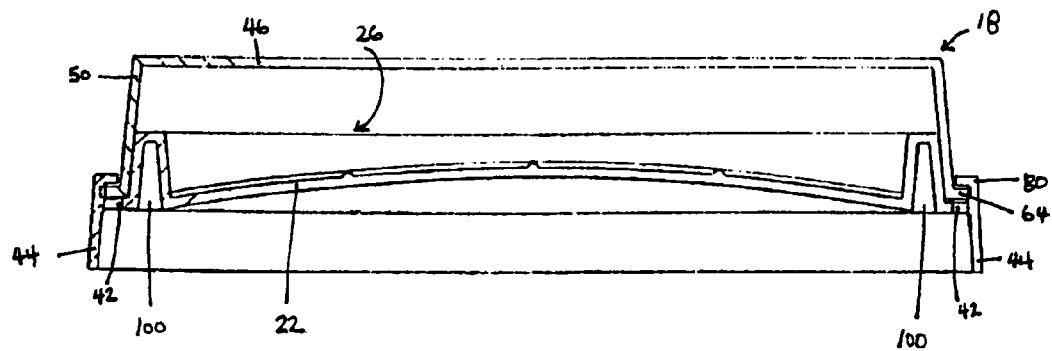
FIG. 4 is a cross-sectional side view of the contact plate of FIG. 1 with the cover and base secured together with the inter-engaging rib and groove arrangement.

As best shown in FIGS. 2, 3, and 4, the cover (18) is positioned over the base receptacle (30) in the closed position. The top wall (46) has a larger diameter than the base side wall (26). The cover side wall (50) is of a size and configuration that it surrounds and overlaps the base side wall (26), wherein the edge (62) of the cover side wall (50) rests on and is supported by the flange surface (43). The cover side wall (50) preferably has a height greater than the height of the base side wall (26).

As shown in FIGS. 1, 2, and 4, the cover (18) and base (14) have a means for releasably locking the cover (18) to the base (14) of the contact plate (10) when the cover (18) is in the closed position, wherein the locking means comprises an inter-engaging rib and groove arrangement. In the embodiment shown in the figures, the cover (18) includes two or at least two outwardly extending ribs (64), which extend outward from the outer surface area (56). The two ribs (64) are preferably disposed opposite each other. Each rib (64) has a first end (68) and a second end (72), wherein the first end (68) has an integrally formed projection (76) extending outwards.

Figure 5:
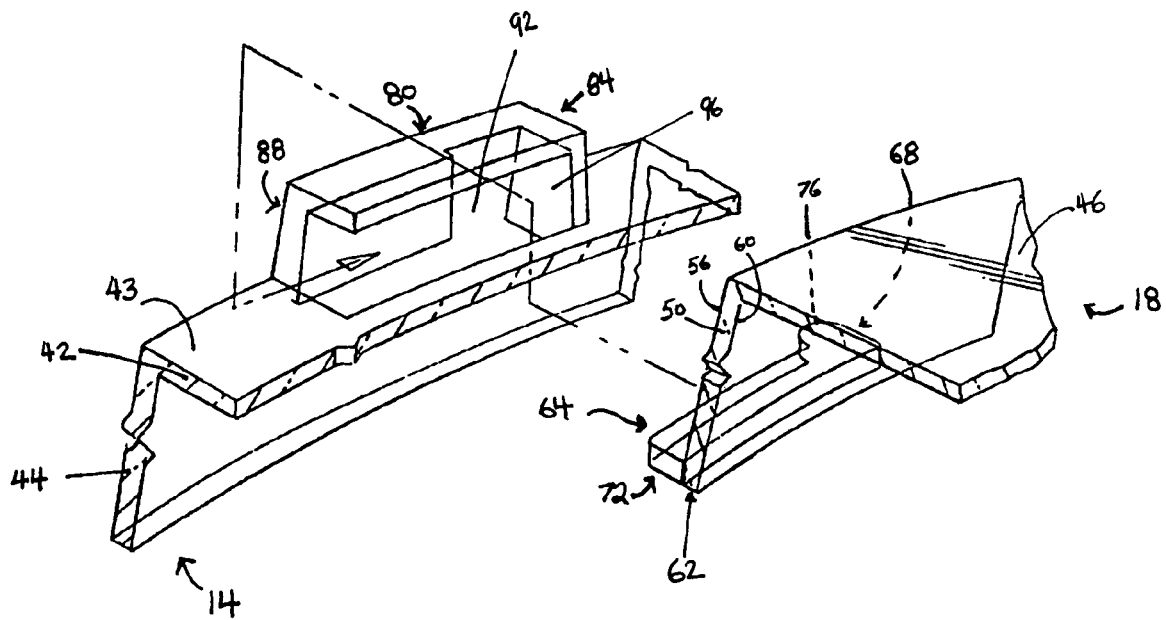
FIG. 5 shows a partial perspective view of a locking means used with the present invention.
Figure 6:
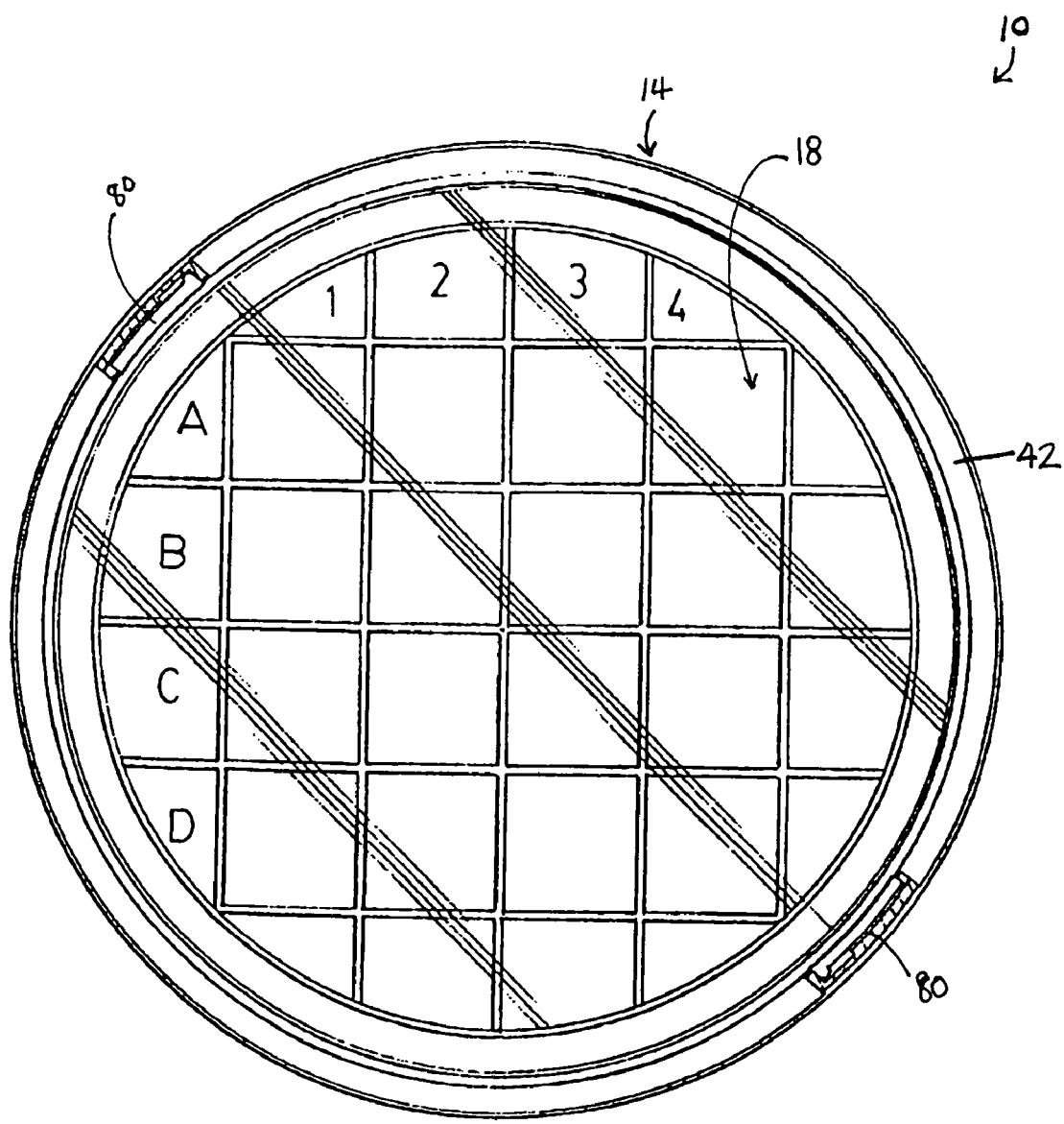
FIG. 6 is a top view of the contact plate of FIG. 1.

In an embodiment as shown in FIG. 5, the flange (42) includes two or at least two integrally formed groove members (80), adapted to slideably receive and hold the ribs (64) in the closed position. Groove member (80) having a first end (84) and a second end (88), comprises a cut-away portion (92) positioned at the first end (84) of groove member (80) and a stop portion (96).

The locking means comprises relative sized ribs (64) and groove members (80) that are oriented in the same clock-sense direction, wherein the rotation of the cover (18) relative to the base (14) in the proper direction will result in each rib (64) seating within the corresponding groove member (80) to position the projection (76) within the cut-away portion (92). When the cover (18) is slightly turned in the opposite direction from the original direction of locking, the projection (76) will disengage from the cut-away portion (92) to release the rib (64) from the corresponding groove member (80).

In an embodiment shown in the figures, the cover (18) fits to the base (14) with the edge (62) and ribs (64) abutting the flange surface (43). The cover (18) is rotated in a clock-wise direction with respect to the base (14), so to slideably position the ribs (64) through the opening in the second end (88) and within the corresponding groove member (80). The stop portion (96) is positioned relative to the position of the cut-away portion (92), and abuts the first end (68) of rib (64) when the projection (76) is within the cut-away portion (92). This prevents further rotation of the cover (18) clock-wise and indicates that the cover (18) is in the locked position. It is further understood that the stop portion (96), cut-away portion (92) of groove member (80) and the projection (76) of rib (64) can be positioned to allow the cover to rotate in the counter-clockwise direction.

Figure 7:
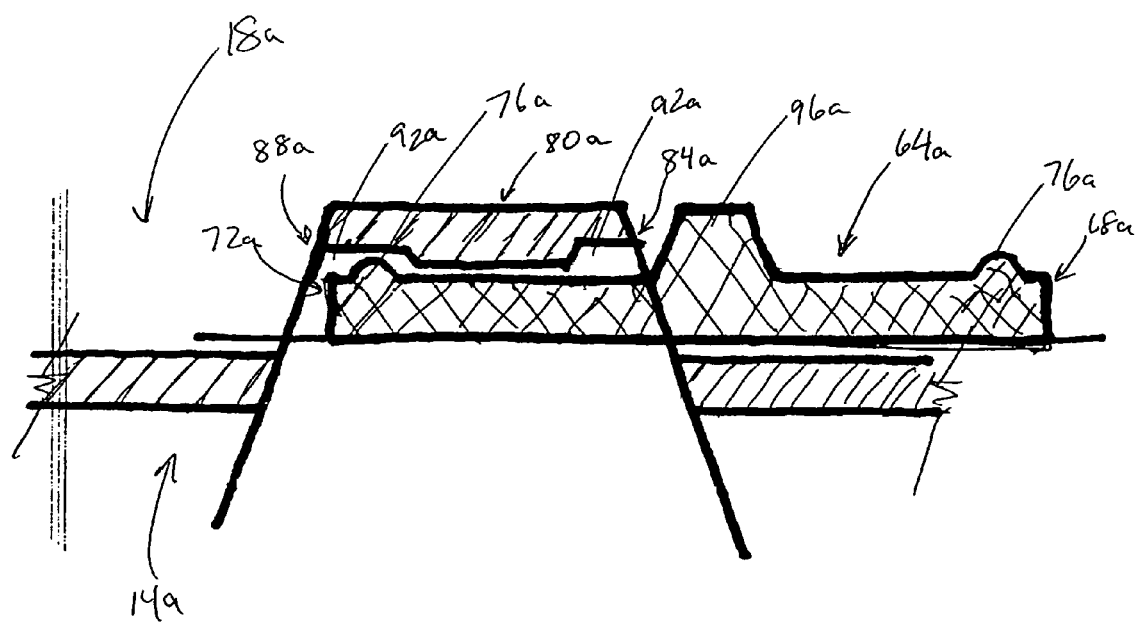
FIG. 7 shows a side elevation view partly in cross section of a second locking means for use with the contact plate of the present invention.

In another preferred embodiment of the invention shown in FIG. 7, the inter-engaging rib and groove arrangement as described may be alternatively arranged whereby the groove member (80a) comprises an open first end (84a) and an open second end (88a), with a cut-away portion (92a) located in close proximity to each first end (84a) and second end (88a). The rib (64a) having an integrally formed projection (76a) affixed at each first end (68a) and second end (72a), comprises an integrally formed stop portion (96a) affixed at the mid-point of rib (64a) which extends radially outwards from the rib (64a). In this embodiment, the cover (18a) can be rotated in either the counter-clockwise or clockwise direction relative to the base (14a) to slideably position the ribs (64a) through the opening in the first end (84a) or the second end (88a) and into the groove member (80a), so that projection (76a) is positioned within the cut-away portion (92a). The stop portion (96a) abuts the ends (84a or 88a) of groove member (80a) indicates that the cover (18a) is in the locked position.

In some applications, it may be desirable to stack a series of contact plates (10) on top of each other. The skirt (44), which surrounds the contact plate (10) and extending downwardly from the perimeter of the flange (42), has a larger diameter than the top wall (46) of the cover (18), thereby providing a means for preventing the shifting of the lower-positioned contact plate. As shown in FIGS. 3 and 4, the base (14) may also include a groove (100) which has the same diameter as the top wall (46) of the cover (18), thereby providing a means for restricting the shifting of the lower-positioned contact plate.

Although various preferred embodiments of the present invention have been described herein in detail, it will be appreciated by those skilled in the art, that variations and modifications may be made thereto without departing from the scope of the appended claims.

The embodiments of the invention in which an exclusive property or privilege is claimed are defined as follows:

1. A contact plate comprising a base and a cover, adapted to be disposed on and enclose at least a portion of the base, each of the base and the cover having a cylindrical configuration, at least one locking means for releasably holding the cover and the base together, wherein the cover is rotated relative to the base to engage the locking means the locking means comprises at least one inter-engaging rib and groove arrangement, the inter-engaging rib and groove arrangement comprises a rib affixed to the outer surface area of the cover, and having at least one radially extending projection; and a groove member affixed to and extending upwardly from the outer surface area of the base and having a corresponding projection-receiving portion; wherein the groove is adapted to slideably receive the rib, so that the projection is positioned in the projection-receiving portion of the groove in the locked position.

2. A contact plate according to claim 1, wherein the inter-engaging rib and groove arrangement comprises: at least one rib affixed to and extending upwardly from the outer surface area of the cover, and having at least one radially extending projection; and a groove member affixed to the outer surface area of the base and having a corresponding projection-receiving portion; and means for indicating when the rib and groove arrangement is in the locked position, which is affixed to either the rib or the groove; wherein the groove is adapted to slideably receive the rib, so that the projection is positioned in the projection-receiving portion of the groove and the rib or groove abuts the indicating means in the locked position.

3. A contact plate comprising a base having a bottom wall and a side wall extending upward from the bottom wall and extending continuously along its entire periphery and attached thereto to form a receptacle; a cover having a top wall and a sidewall extending downwardly from the top wall and attached thereto, said cover configured to fit over and enclose the receptacle; at least one rib affixed to the outer surface area of the cover, and having at least one radially extending projection; at least one groove member affixed to the outer surface area of the base, and having a projection-receiving portion, wherein the groove is adapted to slideably receive a rib; wherein the cover and base rotate relative to each other, so that the groove slideably receives the rib and the projection is positioned in the projection-receiving portion of the groove in the locked position.

4. A contact plate according to claim 3, wherein the base and the cover have a cylindrical configuration.

5. A contact plate according to claim 3, wherein the rib or groove includes a means for indicating that the cover is in the locked position.

6. A contact plate according to claim 5 wherein the indicating means comprises a stop affixed to the groove member for abutting the end of the rib when the projection is positioned in the projection-receiving portion.

7. A contact plate according to claim 5 wherein the indicating means comprises a stop affixed to the rib for abutting the edge of the groove member when the projection is positioned in the projection-receiving portion.

\* \* \* \* \*